United States Patent
Suliman et al.

(10) Patent No.: US 11,607,424 B2
(45) Date of Patent: Mar. 21, 2023

(54) CARBON-RICH MICRO-PARTICLES FOR PROTECTING BEES AND OVERCOMING COLONY COLLAPSE DISORDER

(71) Applicants: WASHINGTON STATE UNIVERSITY, Pullman, WA (US); Waled Suliman, Pullman, WA (US); Brandon Hopkins, Pullman, WA (US); Manuel Garcia-Perez, Pullman, WA (US)

(72) Inventors: Waled Suliman, Pullman, WA (US); Brandon Hopkins, Pullman, WA (US); Manuel Garcia-Perez, Pullman, WA (US)

(73) Assignee: Washington State University, Pullman, WA (US)

( * ) Notice: Subject to any disclaimer, the term of this patent is extended or adjusted under 35 U.S.C. 154(b) by 78 days.

(21) Appl. No.: 16/962,640

(22) PCT Filed: Jan. 18, 2019

(86) PCT No.: PCT/US2019/014224
§ 371 (c)(1),
(2) Date: Jul. 16, 2020

(87) PCT Pub. No.: WO2019/143958
PCT Pub. Date: Jul. 25, 2019

(65) Prior Publication Data
US 2020/0352992 A1 Nov. 12, 2020

Related U.S. Application Data

(60) Provisional application No. 62/619,005, filed on Jan. 18, 2018.

(51) Int. Cl.
*A61K 33/44* (2006.01)
*A23K 50/90* (2016.01)
(Continued)

(52) U.S. Cl.
CPC .............. *A61K 33/44* (2013.01); *A01K 53/00* (2013.01); *A23K 20/163* (2016.05); *A23K 40/10* (2016.05); *A23K 50/90* (2016.05); *A61K 9/16* (2013.01)

(58) Field of Classification Search
CPC ........ A01K 53/00; A01K 51/00; A23K 50/90; A23K 20/163; A23K 40/10; A01N 27/00; A01N 25/14; A61K 9/16; A61K 33/44
See application file for complete search history.

(56) References Cited

U.S. PATENT DOCUMENTS 9,346,678 B1\* 5/2016 Alshehri ............ B01J 20/28004
2012/0171294 A1\* 7/2012 Glenn ..................... A61P 33/14
424/769

(Continued)

OTHER PUBLICATIONS

Brice et al., "Pollen Digestibility by Hummingbirds and Psittacine", The Condor, 91, 681-688 (1989). (Year: 1989).\*

*Primary Examiner* — Jianfeng Song
(74) *Attorney, Agent, or Firm* — WCF IP

(57) ABSTRACT

Compositions and methods for protecting bees from toxins and for preventing or decreasing colony collapse are provided. The compositions comprise carbon microparticles which, when ingested by bees, increase their survival after exposure to toxins such as pesticides.

10 Claims, 9 Drawing Sheets

(51) Int. Cl.
*A23K 40/10* (2016.01)
*A23K 20/163* (2016.01)
*A61K 9/16* (2006.01)
*A01K 53/00* (2006.01)

(56) References Cited

U.S. PATENT DOCUMENTS

2014/0212520 A1 7/2014 Del Vecchio
2017/0151293 A1* 6/2017 Kovarik .................. C12N 1/20

* cited by examiner

CARBON-RICH MICRO-PARTICLES FOR PROTECTING BEES AND OVERCOMING COLONY COLLAPSE DISORDER

BACKGROUND OF THE INVENTION

Field of the Invention

The invention generally relates to compositions and methods for protecting bees from toxins and for preventing or decreasing colony collapse. In particular, the invention provides compositions comprising carbon microparticles which, when ingested by bees, detoxify toxins such as pesticides and increase their chances of survival.

Description of Related Art

The total economic value of honey bee (*Apis mellifera*) pollination worldwide has been estimated to exceed $153 billion, which represents about 10% of the value of global food production. 264 of the crops grown in the world have been identified as being dependent or partially depend on pollination by honey bees. Regionally, honey bee pollination is an essential player in food security in North America, where 90 of the most commercially produced crops are honey bee-dependent. The estimated value of honey bee pollination services for the United States economy is $16.4 billion annually. California's almond industry alone yields 80% of the almonds produced worldwide, is worth 4.8 billion dollars each year, and requires the use of at least 1.4 million beehives to achieve adequate pollination (about 60% of all current U.S. beehives).

The decline in the number of honey bee colonies has raised great public concern worldwide due to the profound and devastating impact on global food security. The number of honey bee colonies in the United States has declined steadily over the past 60 years, from 6 million colonies in 1947 to 4 million in 1970, 3 million in 1990, and just 2.5 million today. These losses threaten the economic viability of the beekeeping industry and have serious implications for pollination services. For example, in the almond pollination services industry, the cost of renting honey bee hives rose from about $50 per hive in 2003 to $175 per hive in 2009.

A prominent problem is colony collapse disorder (CCD) which has killed and continues to kill millions of colonies in the US. The consensus among bee scientists is that massive honey bee colony declines are the results of multiple stress factors working independently, in combination, or synergistically. Examples include pathogens, pesticides, parasitic mites, poor management, landscape alteration, agricultural intensification and competition from non-native species, with pesticides (e.g. insecticides, herbicides, and fungicides) being considered a major factor. Honey bees are exposed to pesticides that are used to control pests and diseases of cultivated plants on which bees depend for gathering nectar and pollen. Exposure also occurs when bees collect water from pesticide-contaminated ponds and streams. Guttation fluid produced from pesticide-treated plants is another source of exposure as is honeydew from aphids which live on systematic-pesticide treated plants. Honey bees are also exposed to pesticides within the hive itself when they are used by beekeepers to treat hives to control parasitic mites and pathogens. Multiple studies conducted in Europe and the U.S. have shown that managed bee colonies generally contain high levels of a wide array of different chemicals in honey, pollen, beeswax, the bees themselves, and even bee semen.

A new class of systemic insecticides, the neonicotinoids (such as imidacloprid, acetamiprid, clothianidin, thiamethoxam, and thiacloprid), are transported to all plant parts via plant sap, thereby providing prolonged plant protection. As a consequence, bees are exposed over long periods of time to neonicotinoid residues in nectar, guttation fluid, pollen, and dust particles. This class of pesticides is still used extensively, even though it has been proven that they exert a neurotoxic effect on bees. For example, even at sub-lethal levels, neonicotinoids have negative effects on honey bee behavior, larval development, learning ability, foraging success, overall physiology and the ability to fight off infections, thereby directly influencing the overall health of colonies. Sub-nanogram toxicity results in failure to return to the hive without immediate lethality, the primary symptom of colony collapse disorder.

While Europe has instituted a ban on neonicotinoids, other countries have not followed suit. Instead, common approaches to this problem take the form of regulations and recommendations made by various agencies. For example, suggested practices include restricting pesticide applications to the evening, removing flowering weeds from cropped areas prior to application, and/or minimizing dust emission. However, these practices are difficult or inconvenient to implement and enforce. Further, the guidelines on which these practices are based usually take into account only lethal levels of one chemical at a time, whereas bees are exposed to multiple agrochemicals while foraging, the combined effects of chemicals can be many times more toxic than that of a single chemical alone, and sublethal doses can be equally damaging.

So far, there is no physical product or practical solution that, at an individual level, protects bees from the deleterious effects of toxin exposure, particularly after they have been exposed to and ingested toxic agents.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Provided herein are compositions and methods for protecting bees from the deleterious effects of exposure to toxins such as pesticides. The compositions comprise carbon-rich microparticles in a carrier that is palatable to and edible by bees, i.e. the compositions are a food source for bees. The methods involve providing food sources comprising the carbon-rich microparticles to bees that have been or are likely to be exposed to toxins such as pesticides, in order to prevent or lessen the harmful impact of pesticide ingestion by the bees. As a result, individual bee health and survival rates are improved, and occurrences of colony collapse are decreased.

It is an object of this invention to provide a method of preventing or treating intoxication of a bee, comprising providing to the bee a comestible composition comprising carbon-rich microparticles (CMPs). In some aspects, the bee is a honey bee. In some aspects, the honey bee is an *Apis mellifera* bee. In further aspects, the intoxication is caused by exposure to at least one herbicide, insecticide or fungicide. In other aspects, the at least one herbicide is a neonicotinoid. In certain aspects, the neonicotinoid is imidacloprid, acetamiprid, The method of claim 6, wherein the source of nutrition comprises one of more of: one or more sugars, honey, one or more proteins and one or more lipids. In additional aspects, the comestible composition is in the form of a liquid, a semi-solid or a solid. In yet further aspects, the CMPs are carbonized bee pollen pellets or carbonized pollen grains. In other aspects, the carbonized bee pollen pellets and/or the carbonized pollen grains are oxidized. In yet further aspects, the carbonized bee pollen pellets and/or the carbonized pollen grains comprise amino and/or nitro functional groups.

Also provided are methods of preventing or treating colony collapse disorder (CCD) in a colony of bees, comprising providing to the bees a comestible composition comprising carbon-rich microparticles (CMPs). In some aspects, the comestible composition is provided in a device that is accessible by the bees. In additional aspects, the step of providing includes placing the device in an orchard or in a hive.

Also provides are compositions comprising bee food, and carbon-rich microparticles (CMPs). In some aspects, the composition is a liquid, a semi-solid or a solid. In further aspects, the liquid is a solution comprising one or more sugars and/or honey. In additional aspects, the composition is in the form of granules or patties. In yet further aspects, the CMPs are carbonized bee pollen pellets or carbonized pollen grains. In additional aspects, the carbonized bee pollen pellets and/or the carbonized pollen grains are oxidized. In yet further aspects, the carbonized bee pollen pellets and/or the carbonized pollen grains comprise amino and/or nitro groups.

Also provided are devices for delivering food to bees, wherein the device comprises a composition comprising bee food, and carbon-rich microparticles (CMPs). In some aspects, the composition is a liquid, a semi-solid or a solid. In further aspects, the liquid is a solution comprising one or more sugars and/or honey. In additional aspects, the composition is in the form of granules or patties. In yet further aspects, the CMPs are carbonized bee pollen pellets or carbonized pollen grains. In additional aspects, the carbonized bee pollen pellets and/or the carbonized pollen grains are oxidized. In yet further aspects, the carbonized bee pollen pellets and/or the carbonized pollen grains comprise amino and/or nitro groups. In some aspects, the device is a container comprising openings to allow bees to enter and exit the container. In additional aspects, the device has at least one external structure that permits the device to be placed in a hive or hung from a tree or pole in an orchard.

Also provided are methods of preparing carbon-rich micro-particles, comprising heating organic micro-particles to at least 500° C. by increasing the temperature of the micro-particles at a heating rate of 5-15° C. per minute; and cooling the micro-particles to room temperature at a cooling rate of 1-5° C. per minute; wherein a residence time of the micro-particles at at least 500° C. is 0, and wherein the steps of heating and cooling are performed in an inert environment. In some aspects, the heating rate is 10° C. per minute. In other aspects, the cooling rate is 2.5° C. per minute. In further aspects, the inert environment is $N_2$ gas. In yet further aspects, prior to the step of heating, the micro-particles are pretreated by one or both of water and ethanol, and then dried. In additional aspects, prior to the step of heating, the micro-particles are sized. In some aspects, the organic micro-particles are bee pollen pellets or pollen grains. In other aspects, the method is performed in the presence of an activation agent. In additional aspects, the activation agent is phosphoric acid.

Also provided are methods of preparing carbon-rich micro-particles, comprising heating organic micro-particles to a temperature of at least 700° C.; maintaining the organic micro-particles at 700° C. for 20 minutes under $N_2$; activating the micro-particles by i) exposing the micro-particles to CO, at 700° C. for 30 minutes, and then ii) contacting the micro-particles with steam at 700° C. for 30 minutes; and cooling the micro-particles to room temperature.

DETAILED DESCRIPTION

Carbonaceous materials (e.g. activated carbon, charcoal, etc.) have been used as a detoxification agent for the management of mammalian patients with drug overdoses and acute poisonings. For example, activated carbon is useful for treating individuals in danger from oral drug overdoses of depressants (such as alcohol, barbiturates, and benzodiazepines), or stimulants (such as ecstasy, cocaine, and amphetamines), or chemical poisons that cause tissue damage. However, a detoxification approach using "cleansing detox-materials" has not been previously described for honey bees.

Figure 1:
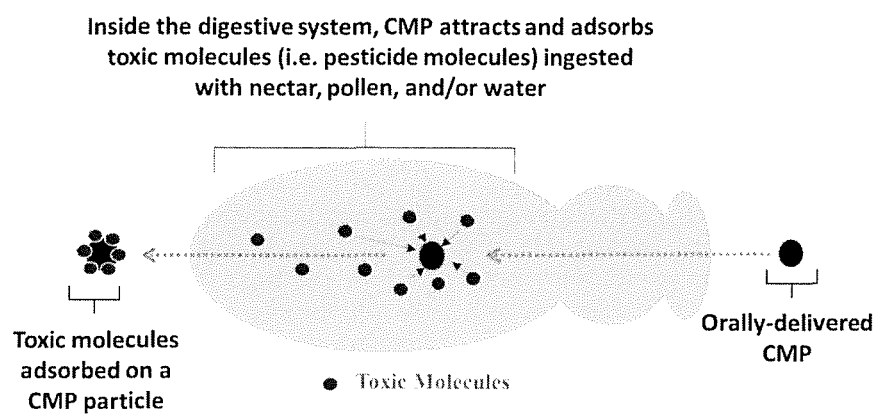
FIG. 1. Schematic illustration of the process described in the disclosure. CMP=carbon-rich microparticle.

The present disclosure provides carbon-rich materials that are designed specifically for oral delivery to honey bees. The carbon-rich materials are generally carbon-rich particles made from pollen grains, bee pollen, cellulosic or other natural materials that are appropriately sized (e.g. micron-sized) for ingestion by bees. The particles pass through the digestive system of the bees without causing harm, and, without being bound by theory, it is believed that in the digestive system, the particles bind to chemicals (e.g. toxins) which the bees have ingested (e.g. toxins in nectar, pollen grains, water, etc). The carbon-bound toxin is then excreted by the bees, and the digestive tract of the bees is thus cleansed and detoxified. A schematic of this process is shown in FIG. 1. Experiments described herein show that providing carbon-rich micro-particles to bees (e.g. in food) increases their chance of survival (decreases the death rate) after exposure to pesticides.

Definitions

Bee pollen: Bee pollen is a ball or pellet (grain, granule, etc.) of field-gathered flower pollen packed by worker honeybees, and used as the primary protein source for the colony. Bee pollen is made from bee saliva, and plant pollens and nectar collected by the worker bees. Each bee pollen pellet contains over two million flower pollen grains. The exact chemical composition depends on the plants the worker bees gather the pollen from. The average composition is said to be 40-60% simple sugars (fructose and glucose), 20-60% proteins, 3% minerals and vitamins, 1-32% fatty acids, and 5% diverse other components.

Pollen or pollen grains: a fine powdery proteinaceous substance, typically yellow, comprised of microscopic grains discharged from the male part of a flower or from a male cone. Each grain contains a male gamete that can fertilize the female ovule, to which pollen is transported by the wind, insects, or other animals. Pollen is produced by seed plants such as trees, grasses, flowers, weeds, etc.

Pollen patty: a supplemental feed provided to the bees and is made up of a wide range of components and concentrations of such components vary widely but is intended to serve as a source of protein. In some cases, the patty might contain no pollen and utilize other materials as a source of protein (eg. brewers' yeast).

Micro-particles: A microparticle is a particle which is from approximately 1 to 1000 micrometers in size. Typical microparticles are from 10 to 250 μm in size, inclusive.

Herbicide: a substance that is toxic to plants and is used to destroy/kill unwanted vegetation.

Pesticide: a substance used for destroying/killing insects or other organisms harmful to cultivated plants or to animals.

Fungicide: a chemical that destroys/kills fungus.

A "carbon-rich microparticle" is a microparticle (generally a microparticle that is formed from organic matter that comprises carbon) that has been subjected to carbonization, i.e. a. process by which solid residues with increasing content of the element carbon are formed from the organic material, usually by pyrolysis in an inert atmosphere. Carbonization is a complex process in which many reactions take place concurrently (e.g. dehydrogenation, condensation, hydrogen transfer and isomerization). The final pyrolysis temperature applied controls the degree of carbonization and the residual content of foreign (non-carbon or complex carbon) species. For example, for the carbon-rich microparticles disclosed herein, the elemental carbon content of the residue is or exceeds a mass fraction of at least about 70 wt %, and may be or exceed 80%.

Mass fraction: the mass fraction of a substance within a mixture is the ratio of the mass of that substance to the total mass of the mixture.

Normal lifespans of bees: The average life span of a queen bee is about 3-5 years. Worker bees that are born during the summer season live for a period of about 6 to 7 weeks and worker bees that are born in the autumn live for about 4 to 6 months. Drones typically live for only a few weeks, e.g. about 4 months maximum.

Compositions and Methods of Making Compositions

The disclosure provides compositions comprising carbon-rich microparticles (CMPs) that are suitable and safe for ingestion by bees. In some aspects, the CMPs are produced by pyrolysis of a natural product such as bee pollen grains and/or pollen. However, the practice of the invention is not limited to the use of only those substances. Other materials that may be used to make CMPs include but are not limited to: various organic woody biomass substances such as wood materials (e.g. saw dust, wood, bark etc.), agricultural residues (e.g. wheat straw, rice husk, corn stove, almond shells, coconut shells, etc.), forest residues (branches, leaves, seeds, poplar wood, pine wood, etc.)

The materials that are used, which are typically particulate materials, may or may not be pre-treated before being converted into a "carbon-rich" form that is suitable for use in a composition. For example, they may be washed one or more times e.g. with a polar solvent (e.g. water, acidic solutions) and/or with a non-polar solvent (e.g. an alcohol such as ethanol) to remove extraneous substances, e.g. dirt, debris, wax, honey, lipids, fats, etc. from the outer surface of the materials.

If needed, the materials may also be sized, e.g. usually reduced in size so that they are "micro-particles" as defined herein. Methods of reducing the size of particulate matter include, for example, grinding, ball milling, etc. The particulate matter may be sized with or without and before or after one or more steps of washing, as described above.

Generally, the size of the microparticles ranges from about 1 to about 1000 micrometers in size, e.g. from about 10 to 900, or about 20 to 800, or about 30 to 700, or about 40 to 600, or about 50 to 500, or about 60 to 400, or about 70 to 300, or about 80 to 200, or about 90 to 100 micrometers. Typically, the particles are about 10 to about 250 micrometers in size.

The particulate matter is subjected to pyrolysis so that the material is at least partially carbonized. Prior to pyrolysis, the sized particulate matter is usually dried, especially if washing (e.g. with water or diluted acidic/basic solution) or chemical pretreatment (e.g. acid impregnation) steps are included.

Pyrolysis of the micro-particulate matter is performed by heating under an inert atmosphere. The micro-particles are generally slowly heated from room or ambient temperature to e.g. at least about 400° C., and usually to at least about 500° C., or even to about 1000° C., e.g. temperatures of about 400, 450, 500, 550, 600, 650, 700, 750, 800, 850, 900, 950, 1000° C. may be used, such as about 700° C. To attain the desired temperature, a slow heating rate is generally used, e.g. from about 5-15° C. per minute, such as about 5, 10 or 15° C. per minute, such as about 10° C. per minute.

Significantly, the present inventors have discovered that it is advantageous to use a residence time of zero at the final temperature, i.e. once the desired temperature is reached, the sample is not maintained at that temperature but instead, cooling at a slow rate is begun immediately. In some aspects, the method is advantageously performed in the presence of an chemical activation agent (such as phosphoric acid). A slow cooling rate is generally in the range of e.g. from about 1 to about 5° C. per minute, such as about 1, 1.5, 2.0, 2.5, 3.0, 3.5, 4.0, 4.5 or 5° C. per minute, such as 2.5° C. per minute, until ambient (e.g. room) temperature is attained. This strategy advantageously minimizes energy consumption. While this is a preferred aspect of the invention, other pyrolysis protocols may also be used, e.g. the sample may be kept at a high temperature of choice for a short period of time, e.g. for about 1-30 minutes, to achieve a desired degree of carbonization, and/or the heating and/or cooling rates may be varied.

In this method, all steps of pyrolysis, including heating and cooling, are performed under inert, non-reactive conditions, such as under nitrogen or another inert gas (e.g. helium, argon, carbon dioxide, or ammonia).

Another method also involves activation of the particles (to form holes) by altering the environment of the micro-particles during processing, rather than introducing a chemical activation agent such as phosphoric acid. In this method, organic micro-particles are heated to a temperature of at least about 700° C. (e.g. about 600 to about 800° C.) and then are maintained at that temperature (e.g. 700° C.) for about 15-30 minutes (e.g. about 20 minutes) under and inert atmosphere such as $N_2$. Following this, the micro-particles are activated by i) exposing them to CO, (still at e.g. 700° C.) for about 20-40 minutes, such as for about 30 minutes, and then ii) contacting the micro-particles with steam (still at about 700° C.) for about 20-4-minutes, such as for about 30 minutes. The micro-particles are then cooled to room temperature for use.

Post-Carbonization Functionalization

The carbon-rich microparticles may or may not be functionalized after pyrolysis and prior to final use in a food for bees. For example, (e.g. dried and cooled) CMPs may be oxidized e.g. by exposure to oxygen (such as by exposure to $O_2$ gas, air, air supplemented with $O_2$, etc.) at an elevated temperature (e.g. at about 150-350° C., such as at about 150, 200, 250, 300 or 350° C., such as about 250° C.). Alternatively, other suitable oxidation/activation methods include: steam, carbon dioxide, chemical activation, etc.

In addition, pre-treating pollen grains with ethanol creates holes and/or large pores (channels) in the grains. Amino and/or nitro groups may be introduced on and/or into the CMPs e.g. by combining the CMPs with a sufficient quantity of yeast cells (e.g. *Saccharomyces cerevisiae*) in a suitable solution and under conditions that allow the yeast cells to attach to the CMPs and/or to enter the holes and pores of the CMPs. Suitable solutions for the growth of yeast in and on the CMPs generally include those with a food source for the yeast (e.g. a sugar), and a pH near neutrality (e.g. about 6.5 to about 7.5, such as about 7.0 or 7.2. To ensure that yeast cells enter at least some of the ethanol-created holes, the yeast cell-CMP mixture can be thoroughly mixed, e.g. by agitation, sonication, ultrasonic treatment, etc. The yeast cells and CMPs are allowed to incubate together e.g. at about 25-30° C. for e.g. about 8-36 hours, such as for about 24 hours. Thereafter, the liquid solution is removed from the CMPs (which contain attached yeast cells), the CMPs are dried and the CMPs are then subject to pyrolysis in an inert atmosphere (e.g. under $N_2$ gas) at a low pyrolysis temperatures. Exemplary low pyrolysis temperatures for this purpose include but are not limited to temperatures of from about 200 to 400° C., such as about 200, 250, 300, 350 or 400° C., such as about 300° C.

CMPs in Food for Bees

For presentation to bees, the carbon micro-particles are generally mixed with a food source for the bees. Examples of food sources that are attractive to bees and safe for them to ingest include but are not limited to: honey; pollen patty; dry white sugar; syrup made from white sugar; high fructose corn syrup; various monosaccharide sugars such as glucose and fructose; disaccharide sugars such as sucrose, maltose and trehalose; etc. The compositions may be in any of several forms, including but not limited to: liquids, solids, semi-solids, etc. and may be shaped e.g. into patties, pellets, granules, etc. The micro-particles may be added to various commercial formulations that are used to provide food to bees. The compositions optionally also include other bee nutrients such as honey, bee pollen, pollen, artificial pollen substitutes (which usually contain sugars and protein), protein supplements, lipid or fatty acid supplements, probiotics, etc. If the compositions are in the form of e.g. granules, pellets, a concentrated liquid, etc. they may be suitable for dispersion in a liquid (e.g. a sugar solution, honey, etc.) or for mixing with a semi-solid or other form of bee food, prior to being provided to bees. Alternatively, the CMPs may be provided separately for use by an end-user e.g. by dispersing, suspending or mixing the CMPs into a liquid, a semi-solid, etc. prior to providing the liquid, semi-solid, etc. to bees.

For sugar solutions, the amount of sugar is generally in the range of from about 20 to 60%, such as about 20, 30, 40, 50 or 60%, w/v of the liquid the sugar is dissolved in (e.g. water).

The amount of CMPs that are included in a composition range from e.g. about 0.1 to about 5%, such as about 0.1, 0.5, 1.0, 1.5, 2.0, 2.5, 3.0, 3.5, 4.0 or 5.0%. Generally, the amount is e.g. from about 0.5 to about 1.5%, such as about 1%.

Devices

Also provided are devices (e.g. feeders) which comprise the compositions described herein. The devices comprise, e.g. a container for containing the compositions, the container being designed so as to allow access to the composition by bees (e.g. the container may contain openings through which the bees enter and leave). The container may be suitable to insertion into a hive, or may be suitable for positioning near a hive or hives, or near a natural food source for the bees, e.g. in an orchard or field with crops that are pollinated by the bees. The device may comprise an external structure that is a means of attaching the device e.g. in or on a hive, or attaching or suspending the device from a tree or pole, e.g. in an orchard. The container may have an open architecture, e.g. similar to a saucer, or may have an enclosed structure with openings that allow ingress and egress by bees, e.g. with windows, slots, or other apertures that allow the bees to enter and exit the container, and optionally to prevent access to the composition by other species, especially non-pollinating species, if possible. The composition may be positioned directly in the container or attached to or positioned on a substrate (e.g. an inert substrate or carrier) within the container, or a "container" may be a substrate. The containers may be disposable (single use) but are preferably multi-use and can be refilled with the composition, and/or new substrates with fresh composition may be inserted into the container when an old substrate is spent (most or all of the composition has been consumed by the bees) and removed.

The devices may be suitable for hanging, e.g. from the branches of trees in an orchard, or from posts, etc., or attaching to trees or posts, e.g. by means of an adhesive. Alternatively, purpose-made holders for the containers may be more or less permanently attached to trees, posts, etc. and the containers may be configured so as to attach to the holder and be detached and replaced after use.

Types of Bees that are Treated

Any of the many known bees may be treated using the methods and compositions described herein. Typically, the bees are "honey bees", i.e. members of the tribe Apini, which contains three clades: *Micrapis* (dwarf honey bees), *Megapis* (giant honey bee), and *Apis* (domestic honey bees and close relatives), including but are not limited to: *Apis mellifera* (also called the western or European honey bee); *Apis cerana indica*, *Apis florea*, *Apis andreniformis*, *Apis dorsata* (including *Apis dorsata binghami*, *Apis dorsata laboriosa*); Eastern *Apis* species such as *Apis koschevnikovi*, *Apis nigrocincta*, and *Apis cerana*; Borneo honey bee *A. cerana nuluensis*; Koschevnikov's bee (*Apis koschevnikovi*); Philippine honey bee (*Apis nigrocincta*); the Eastern honey bee proper, *Apis cerana*, and the subspecies *A. c. indica*; as well as breeds, lineages and sub-species thereof, e.g. the Buckfast bee.

While in some aspects, the insects that are treated as described herein are honey bees, the compositions and methods can be used to prevent and/or treat intoxication in a wide variety of insects. The types of bees treated are not be limited to bees in the tribe Apini. The compositions and methods can also be used for feeding/treatment/protection of bees in the entire superfamily Apoidea. These include exemplary bee species in the genus *Bombus* (bumble bee), the family Halictidae which includes alkali bees, Megachilids like the leaf cutter bee and blue orchard bee, and stingless bees such as Meliponini and carpenter bees. These are just a few examples of the managed species within the more than 20,000 species of bees in the super family Apoidea, any of which can be treated as described herein. In fact, the treatment of any managed and/or desirable population of insects (e.g. flies, moths, butterflies, etc.) that can be impacted and intoxicated by e.g. pesticides, herbicides and/or fungicides, and which are capable of feeding on compositions comprising the CMPs described herein, is encompassed herein.

Methods of Protecting Bees

Methods of treating or preventing intoxication of bees, e.g. intoxication by exposure to at least one herbicide, insecticide and/or fungicide, such as a neonicotinoid (e.g. imidacloprid, acetamiprid, clothianidin, thiamethoxam, thiacloprid, etc.). The methods involve providing CMPs as described herein to the bees, e.g. via a feeding device that the bees easily enter, feed in, and then leave to return to the hive or to other food sources, such as flowers. The method include features of extending the life span of bees that are exposed to toxins (e.g. by extending their life spans to a normal range, and/or increasing their abilities such as the ability to climb, to forage, to locate the hive/nesting site, etc. The methods also are a means of decreasing the mortality rate of foraging bees exposed to toxins and/or of increasing the longevity of such bees. The methods thus protect the bees from the deleterious effects of toxin exposure, such as damaging neurotoxic effects.

In general, as used herein, the terms "treatment" or "treating" relate to but are not limited to prophylactic treatment and therapeutic treatment. As such, the terms "treatment" or "treating" may or may not include, and are not limited to: preventing a condition or the development of a condition (such as intoxication); inhibiting the progression of a condition; arresting or preventing the further development of a condition; reducing the severity of a condition; ameliorating or relieving symptoms associated with a condition; and causing a regression of a condition or one or more of the symptoms associated with a condition of interest.

Considered collectively, for a group of bees that are exposed to a toxin, administration of CMPs generally increases the % of bees that survive by at least about 1-50%, such as by about 1, 2, 3, 4, 5, 6, 7, 8, 9, or 10% or more, such as by about 7%; or by about 10, 15, 20, 25, 30, 35, 40, 45 or 50%, compared to toxin-exposed, untreated bees. Further, the longevity (average life span) of bees and/or the ability of bees to perform normal tasks such as climbing, foraging, etc. is increased by at least about 1-50%, such as by about 1, 2, 3, 4, 5, 6, 7, 8, 9, or 10% or more, such as by about 7%; or by about 10, 15, 20, 25, 30, 35, 40, 45 or 50%, compared to toxin-exposed, untreated bees. The final life span and/or abilities of the bees may or may not attain a level or range that is normal for bees that are not exposed to toxins, but is nevertheless advantageous for maintaining hives and the ability of the bees to successfully pollinate crops.

Methods of Treating or Servicing Crops

The methods, compositions and devices described herein may be used to increase pollination of any of many suitable crops. Examples of such crops include those that are entirely or partially pollinated by bees such as honey bees, including but not limited to: okra, kiwifruit, onion, cashew, celery, starfruit, beet, mustard, rapeseed, broccoli, cauliflower, cabbage, Brussels sprouts, Chinese cabbage, turnip, canola, peas (e.g. Pigeon pea, Cajun pea, Congo bean), peppers (e.g. chili pepper, red pepper, bell pepper, green pepper), papaya, safflower, caraway, chestnut, watermelon, tangerine, orange, grapefruit, tangelo, coconut, coffee spp., coriander, cantaloupe, cucumber, squash, pumpkin, gourd, marrow, zucchini, guar bean, quince, lemon, lime, hyacinth bean, persimmon, cardamom, loquat, buckwheat, fennel, strawberry, cotton, sunflower, flax, lychee, lupine, macadamia, apple, mango, alfalfa, avocado, lima bean, kidney bean, haricot bean, Adzuki bean, mungo bean, string bean, green bean, scarlet runner bean, allspice, apricot, sweet cherry, sour cherry, plum, almond, peach, nectarine, guava, pomegranate, pear, black currant, red currant, rose hips, boysenberry, raspberry, blackberry, elderberry, sesame, rowanberry, hog plum, tamarind, clover (such as white clover, alsike clover, crimson clover, red clover, arrowleaf clover, cranberry, broad bean, cowpea, black-eyed pea, black-eye bean, grape, almond, etc.

Methods for maintaining or increasing pollination of such crops include, for example, providing bees such as honey bees access to the crops and, simultaneously, providing the bees with a composition as described herein. The step of providing the composition to bees that have access to the crops detoxifies toxins that have been or will be ingested by the bees while pollinating the crop, and extends the life span of the bees (e.g. enables the bees to at least live out a normal life span, or at least to extend the life span compared to bees that are not treated) and/or decreases the number of bees that die due to pesticide exposure, as well as enables bees to navigate to their foraging ways normally by reducing the neuro-effect of pesticides, thus maintaining or increasing the amount or level of pollination that the bees can perform.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLE

The effectiveness of any activated carbon (AC) in accelerating drug clearance or adsorbing chemicals from aqueous phase (either in-vivo or in-vitro) is dependent on several factors, including:

(1) AC preparation methods and conditions (e.g. feedstock type, carbonization, activation conditions, residence time, heating rate, etc.);
(2) AC properties (such as surface functionality, porosity, ash content, surface charge, etc.);
(3) adsorbate-related factors (type, concentration, pH, charge, etc.);
(4) contact time between the AC surface and adsorbate molecules; and
(5) environment-related factors (pH, temperature, etc.).

In the absence of data concerning the palatability, toxicity, delivery method, particle size, chemical properties, and effectiveness of carbon materials on honey bees, we conducted a study using bee cages to examine these factors. Palatability and toxicity of carbon-rich micro-particles (CMPs) was examined, and the studies determines whether orally delivered CMPs could act as a gastrointestinal adsorbent and inhibit the absorption of pesticide molecules in the digestive system of bees.

Materials and Methods

Novel carbon-rich micro-particles (CMPs) were prepared from bee-pollen grains using a new carbonization approach at zero residence time in a presence of activation agent. Bee pollen grains were utilized as the carbon precursor and the carbons derived therefrom were oxidized using hot air or N-functionalized using yeast cells. The synthesis of CMPs was done in a way that does not destroy the original architecture of the pollen grain. The overall method is "green" in that no corrosive or toxic chemicals are use. The technique is readily adapted for mass production.

Preparation of Carbon Micro-Particles (MCPs)
Pre-Treatment of Precursor Material Bee pollen grains were divided into two groups. In the first group, pollen grains were left as received with no pretreatment, while in the second group, pollen grains were pretreated first with deionized water to remove any soluble fractions and then with ethanol to remove oily impurities or lipids on the surface. The pretreatment process used is as follows:

50 grams of bee pollen grains were first immersed into deionized water (100 mL) and agitated for 10 minutes. 200 mL of ethanol was then added into the water-pollen mixture with ultrasonic treatment for 1 hour. The ethanol-water-pollen mixture was left 5 hours at room temperature. Pretreated pollen grains were filtered and dried at 25° C. for 72 hours. With this process, individual pollen particles detach from the bee pollen grains and form a uniform powder, minimizing the need for strong mechanical grinding which can destroy pollen architecture.

Production of CMPs 7-10 grams of treated or untreated bee pollen grains were loaded into a quartz boat, placed in a 3-zone tubular furnace (Lindberg/Blue M™) and left under a flow of nitrogen gas (0.5 L min$^{-1}$) for 60 minutes at 25° C. to purge air from the system. The samples were then heated under $N_2$ flow at a constant heating rate of 10° C. min$^{-1}$ to the target carbonization temperature (700° C.), and then kept at this temperature for the target activation period. In this study, three series of CMPs were obtained:

Series I: In order to minimize energy inputs, the system was optimized to be operated at zero residence time (0-RT) in order to minimize energy consumption while maximizing the process performance in terms of product development. This approach has not been reported before. All reported carbonization methods use different lengths of residence time starting from 15 minutes to several days. This 0-RT carbonization method starts with heating up the material at 10° C. min-1 to 700° C. for zero minutes and ends with cooling rate of 2.5° C. min-1. At the end of each run, the sample was kept in the furnace to cool down to room temperature under the same flow of nitrogen, ensuring that the whole process, including heating-up and cooling-down steps, was performed in an inert environment. To obtain acceptable porosity and surface area at 0-RT, dry-impregnated samples at phosphoric acid/pollen mass ratios of 0.5 (P/L ratio) were used. The carbonization and activation processes were carried out at 500° C. and during cooling phase from 500-400° C.

Series II: In order to enhance porosity without a chemical agent, carbonization and activation were carried out through a combination of two physical activation agents; carbon dioxide and steam. The carbonization was carried out with untreated samples at 700° C. for only 20 minutes under flow of nitrogen of 0.5 L·min$^{-1}$ followed by an activation step in which then samples were brought into contact with $CO_2$ (1 L·min$^{-1}$) for 30 minutes and then steam for 30 minutes at 700° C. The total RT here is 80 minutes.

Series III: N- and O-functionalized CMPs: Pre-treating pollen grains with ethanol can create holes in each grain.

Amino/nitro groups were introduced onto the surface of CMPs by growing *Saccharomyces cerevisiae* yeast within pre-treated micro-particles and carbonizing them at a low pyrolysis temperature of 300° C., as follows: 1 gram of dry food-grade Brewer's yeast was immersed in 10 mL of a sucrose solution (5 wt./v. %) and incubated at 28° C. for 30 minutes (activation period). 25 grams of N-CMP was placed in 250 mL flask and sufficient deionized water was added to produce 120 mL of aqueous carbon particles. 5 ml of yeast suspension was mixed with the aqueous carbon particles and then incubated at 28° C. for 24 hours after adjusting the pH to 6.5.

Figure 2:
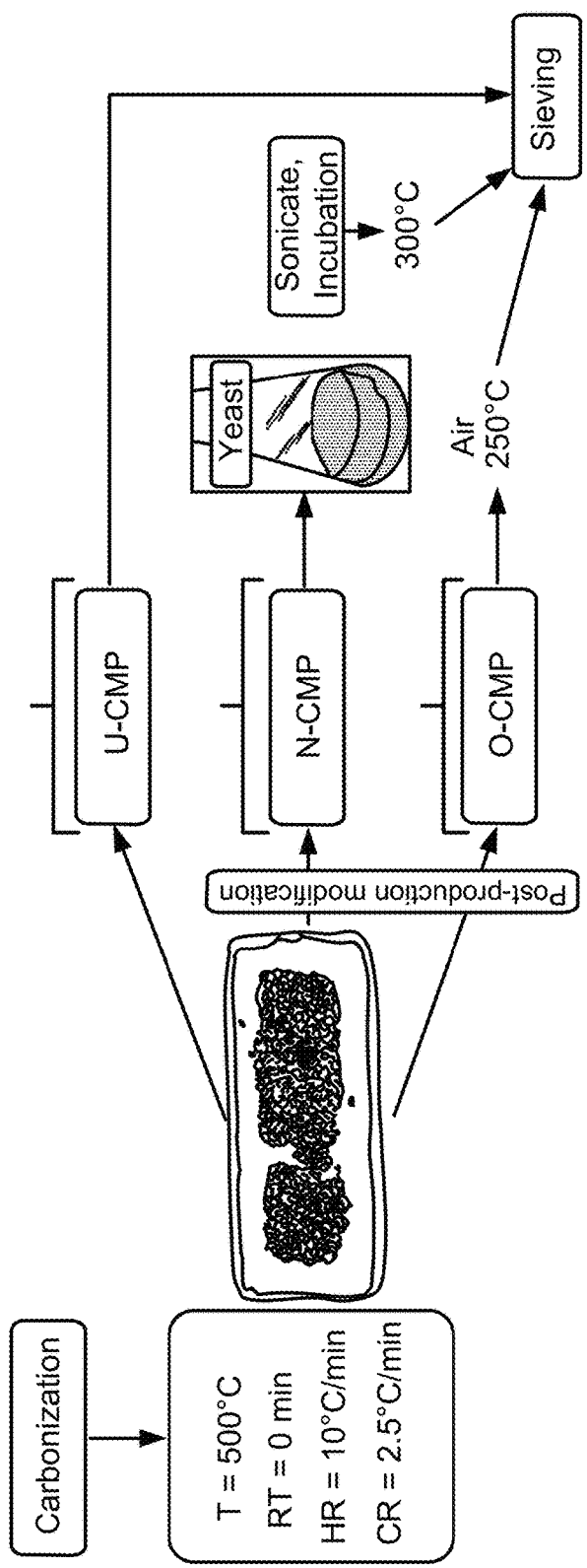
FIG. 2. Schematic illustration shows CMP production and post-production conditions.

To ensure that yeast cells entered the ethanol-created holes, ultrasonic treatment for 1 hour was used prior to filtration. Thereafter, carbon micro-particles with yeast cells were dried and pyrolyzed at 300° C. under nitrogen. The prepared carbon microparticles were characterized by surface area analysis, pH meter, scanning electron microscope (SEM), following procedures similar to those reported in Suliman et al., (2016b). For the oxidation step, the ethanol-pretreated carbonized pollen grains were oxidized by air at 250° C. following a similar method such as, for example in Suliman et al., 2016a. Briefly, CMPs produced from unpretreated pollen grains were left with no post-carbonization treatment and are referred to herein as U-CMP. In contrast, the CMPs produced from ethanol-pretreated pollen grains were further treated in two subgroups: (1) oxidized carbon microparticles (O-CMP), and (2) nitrogen-doped carbon microparticles (N-CMP) (FIG. 2). Briefly, the CMPs were produced by carbonizing bee pollen grains (pre-treated or not with ethanol) and activated using different activation methods based on target residence time. The carbonized pollen grains were then functionalized with oxygen function groups using air at 250° C. and/or with nitrogen functional groups by growing yeasts inside the carbonized-pollen grains.

Figure 3:
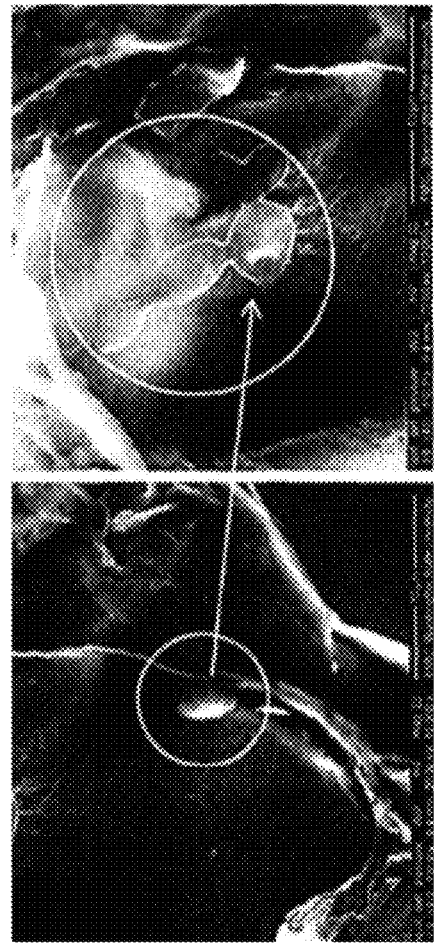
FIG. 3. SEM scans showing that *Saccharomyces cerevisiae* cells attached to and grew on the surface of the carbon-rich micro-particles. The right panel is a close-up of the left panel.

Scanning electron microscopy (SEM) analysis revealed that yeast cells were successfully grown inside the pores of carbonized particles. The SEM images in FIGS. 3A and B show that a yeast biofilm formed on N-CMPs surfaces.

Experimental Design

Figure 4A:
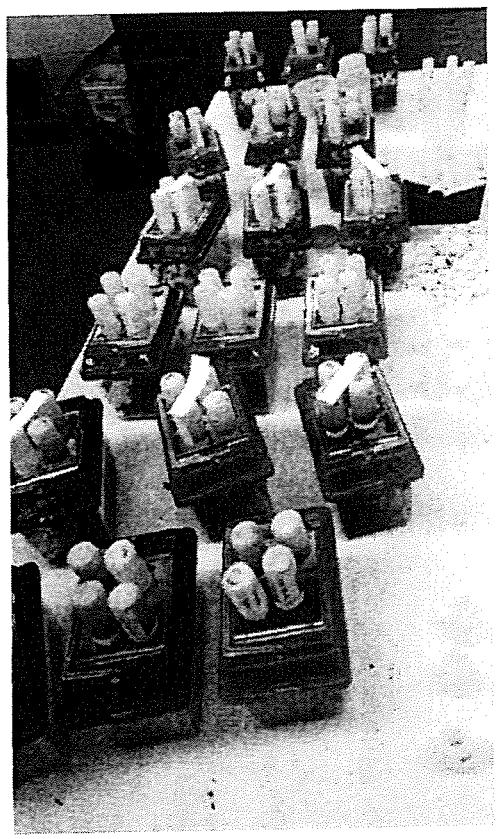
FIGS. 4A and B. Plastic cages used in the study with 100 bees per cage. A, top view of cages; B, close-up of cages.
Figure 4B:
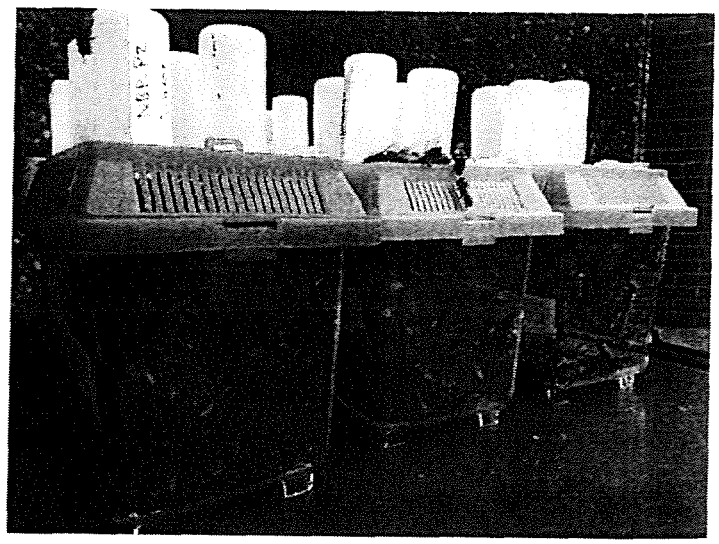

A total of 70 plastic cages (15 cm×8 cm×10 cm) with a removable cover were used FIGS. 4A and B). Adult honey bees were collected from broods of at least seven colonies and homogenously distributed in all control and experimental cages to eliminate possible colony-level effects on the results. Cages were loaded with 100 bees per cage and then incubated in complete darkness at 30° C. and 70% relative humidity (RH). Bees were fed a sugar solution (50% w/v). The CMPs were administered at a concentration of 1% w/v in the sugar solution and delivered to experimental cages on day 2. Stock solutions of Thiamethoxam (TXM) (3-[(2-Chloro-1,3-thiazol-5-yl)methyl]-5-methyl-N-nitro-1,3,5-oxadiazinan-4-imine) were prepared from analytical grade TMX (Sigma Aldrich 37924-100MG-R) at concentration of 30 mg/L in E-pure water, and maintained at 4° C. The pesticide was administered at a concentration of 50 ppb on day 2. The pesticide concentration was chosen higher than typical in-field concentrations to assess the die-off rates within a shorter period of time and to mimic the worst-case scenario in which worker bees are chronically exposed pesticide-contaminated nectar in the field. First, a set of lab-based cage studies were conducted to assess the palatability and impacts of CMPs on honey bees activity, behavior, and mortality rate in the absence of pesticide or other stressors. The second set were designed to study whether the CMPs can increase the survival rate of thiamethoxam-treated bees and reduce the neuro-effect of neonicotinoids. Thus, we tested the chronic effects of TMX on adult bees in the presence and absence of CMPs; continuous exposures over different days of exposure (from $2^{nd}$ to the $7^{th}$ day) would affect survivability, and the ability to climb and fly.

Treatments were arranged in a completely randomized design. For the whole study, four control sets per experiment were used; first control set is 3 cages fed on sugar syrup only, second set control is 3 cages fed on commercial activated carbon (corn-AC) mixed with sugar syrup, third control set is 3 cages fed on CMPs mixed with sugar syrup, last control set is 3 cages fed on sugar syrup spiked with the pesticide. The mortality rates and feed consumption were recorded daily. Production and morphology of bee feces (frass) were assessed to ensure that CMPs passed through the bees digestive system with no harm. Bee behavior and activity (i.e. number of falls per 30 seconds, inability to climb, etc.) were also assessed. Dispensability of the CMPs in the sugar solutions were also assessed during the experiments.

RESULTS AND DISCUSSION

Figure 5A:
FIG. 5A-C. Dispensability behavior of A, N-CMPs, B, O-CMPs, and C, U-CMPs after 24 hours in a 50 wt. % sugar solution.
Figure 5B:
Figure 5C:
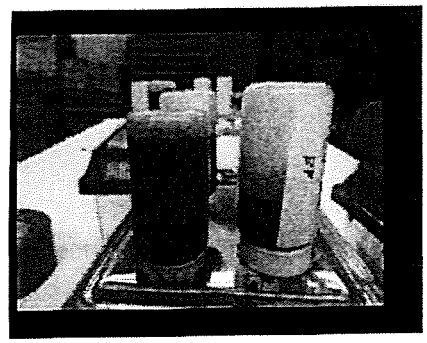
Figure 6A:
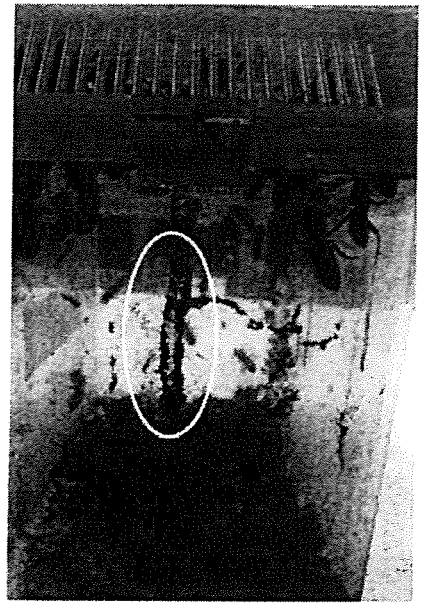
FIGS. 6A and B. Bee feces (frass) production. Blackish-colored samples in a first cage (A) and a second cage (B) confirm successful passage of CMPs through the bee digestive system.
Figure 6B:

Dispersion behavior of the carbon microparticles is very important factor in determining how long the CMPs could be spread evenly throughout the dispersion medium (here, 33% sugar solution). The results are presented in FIGS. 5A-C and showed that O-CMPs and N-CMPs started to settle out upon standing after 24 hours, and completely settled by day 3 (after 72 hours). However, untreated CMPs exhibited better dispersion than O-CMPs and N-CMPs. Commercial activated carbon was not well dispersed compared to the CMPs that were tested; it started to settle after only 1 hour (FIG. 5).

Impacts of CMPs on Bees' Activity and Behavior

Palatability of CMPs

The results showed that bees accepted all carbon microparticle types introduced at a concentration of 1% (w/v). No cages showed any evidence of feed rejection or lower uptake due to the carbon addition. No significant differences were found in the uptake across all particle-sugar mixtures used in this study. Moreover, the honey bees consumed at least 75% of the carbon particles delivered in the sugar solution (not shown).

However, despite similar acceptance endpoints among treatments prior to pesticide exposure, the higher uptake rates of commercial AC apparently weaken bees, e.g. during day 3 of application. This could be related to toxicity of the AC used and/or the faster sedimentation rate (compared to U-CMPs) which resulted in a higher than expected uptake of carbon as time progressed, resulting in lower survival at the end compared to control and CMP fed bees.

Bee Feces (Frass) Production and Morphology

Carbon particles are safe for beekeeping practices if they pass through the digestive system of the bee without killing the bee, changing the bee's behavior, or causing any symptoms of weakness. Cage inspections of bee frass showed normal frass production and morphology with black residues after carbon particles were introduced to the bees. FIGS. 6A and B show signs of successful production of darker than usual frass by the treated bees. A comparison of frass production in cages fed on carbon-sugar solutions and control cages showed no differences in production rate, amount, or morphology (except the color) of bee frass. However, the activity of the bees exposed to commercial AC was lower than that of control bees, especially on day 3, possibly due to physical (e.g. sharp micro-edges) and/or chemical properties (e.g. silica content) of the commercial AC used.

Toxicity of CMPs

Figure 7:
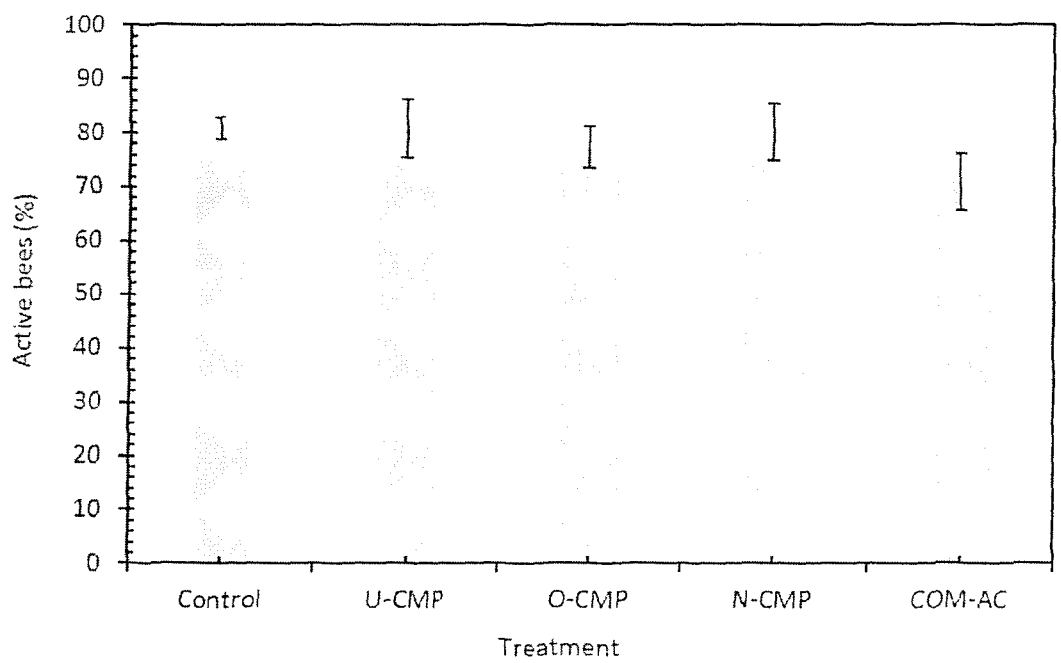
FIG. 7. Survival on day 3 of bees fed on sugar solutions mixed with 1% CMPs.

This study provided evidence for the safe use of some carbon particle types in the diet of adult bees. In particular, results obtained using pollen-derived CMPs showed that ingestion of the CMPs did not result in negative impacts on bee behavior or activity in terms of movement, loss of focus, aggressiveness, or weakness. As seen in FIG. 7, there were no significant differences in bee survival across all treatments after 72 hours of exposure to carbon particles. An exception can be made for cages fed on commercial AC-sugar solution, in which slight weaknesses were observed, especially in day 2, as well as lower survivability (70% survival) compared to the control (82% of active bees). Thus, feedstock selection and production conditions are important factors in determining the characteristics of carbonaceous materials provided to bees. Carbon particles derived from bee pollen grains (CMPs) showed neutral (no deleterious) effects on bee activity and behavior (80-84% of bees remained active after ingestion) compared to the control (82% of bees remained active after ingestion).

Detoxification Effects of the CMPs

Figure 8:
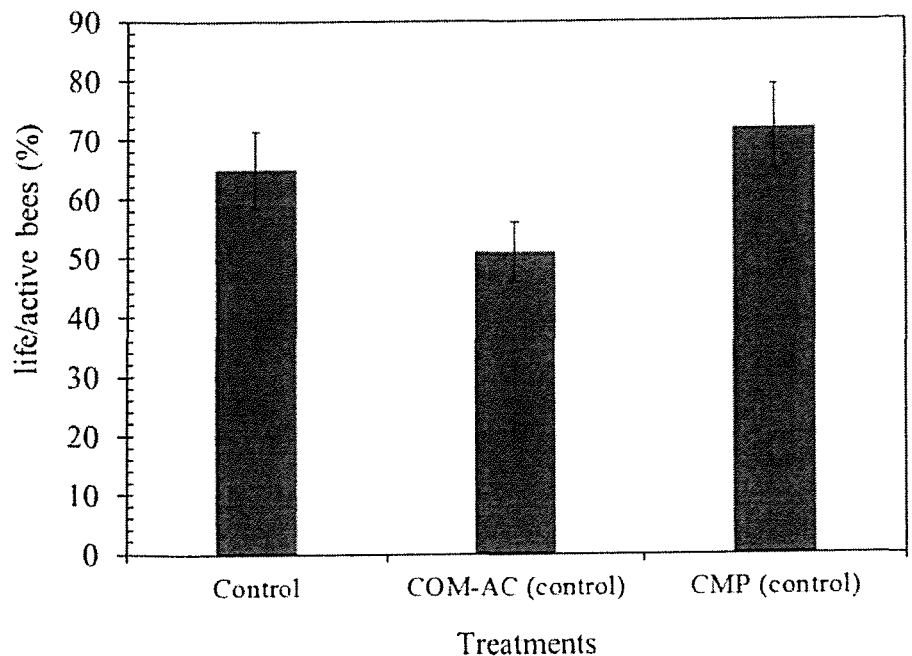
FIG. 8. Survival on day 4 of bees fed on sugar solutions mixed with 1% CMPs or commercial activated carbon (COM-AC).

FIG. 8 shows the effects of pollen-derived CMPs and commercial AC on survival at day 4. As can be seen, cages treated with commercial AC represented a worst-case scenario of exposure to carbon particles (only 50% of the bees survived) compared to the control (in which 65% survived). In contrast, the pollen-derived CMPs enhanced the survivability of bees (72% survived), 7% greater than survival of the controls (n=3).

Figure 9:
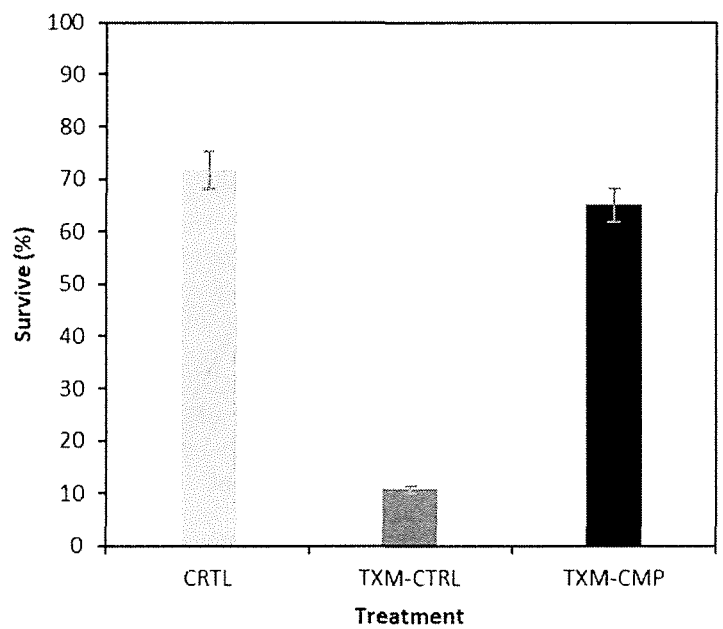
FIG. 9. Cumulative survival rate of adult bees chronically exposed to 50 ppb Thiamethoxam in 50% sugar solution. Bees were fed with CMPs in a 50% sugar solution prior pesticide exposure. CTRL=control (no TXM nor CMP), TXM-CTRL=cages exposed to TXM in sugar solution, TXM-CMP=cages exposed to TXM after been fed on CMPs.
Figure 10:
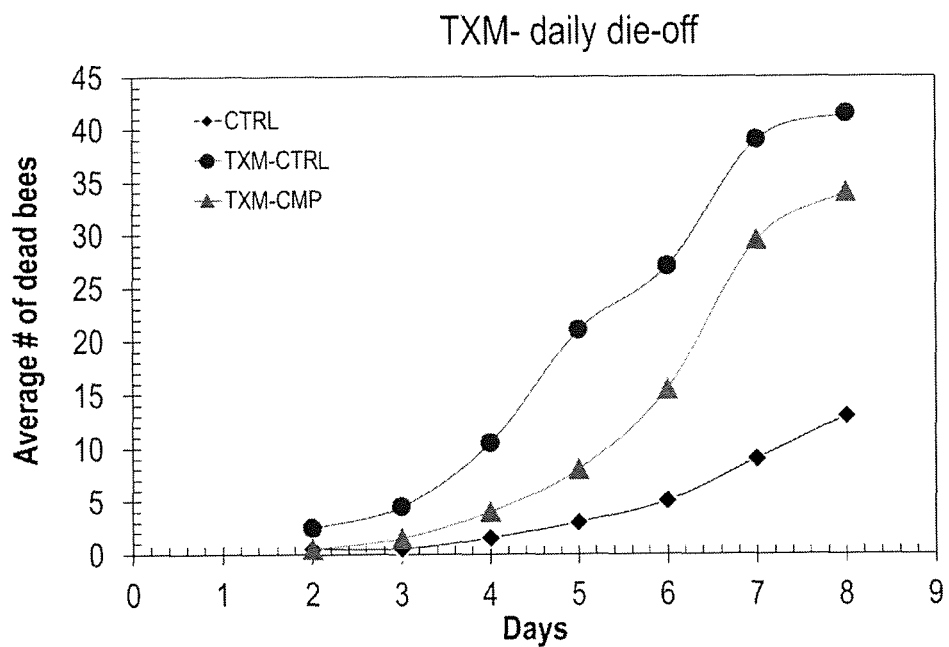
FIG. 10. Effect of TXM on the die-off rate (daily basis) in presence of CMP (TXMP-CMP, triangles) and absence of CMPs (TXM-CTRL, circle).
Figure 11:
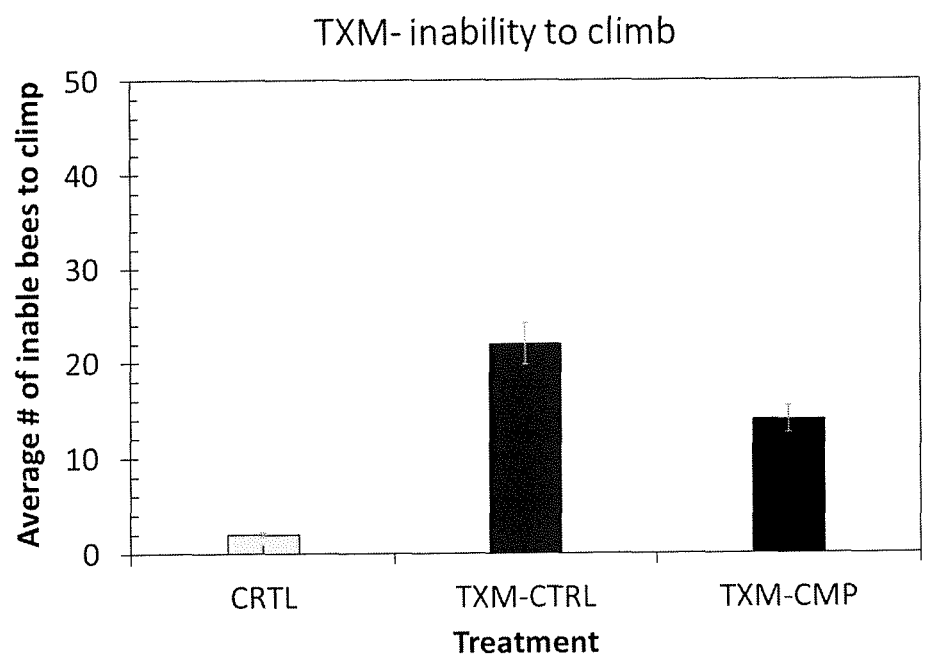
FIG. 11. Effect of TXM on bee activity.
Figure 12:
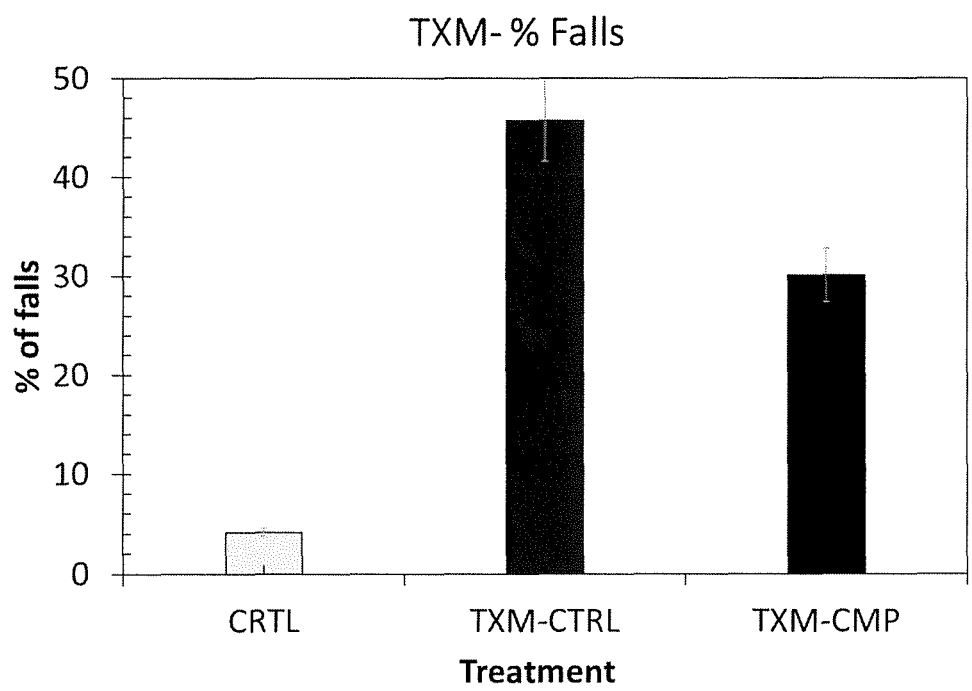
FIG. 12. Effect of TXM on bee activity.

The mortality rate and longevity of adult bees exposed orally to 50 ppb Thiamethoxam (TXM) in the presence of CMPs, commercial AC or no carbon particles (control) was examined. This study involved intestinal exposure of the bees to toxic molecules in contaminated feed (a 50% sugar solution). The results showed that damage to bees was minimized by feeding them pollen-derived CMPs. As seen in FIG. 9, results obtained from bee cages fed on pollen-derived CMPs and then exposed to the insecticide showed that CMPs prevented death and saved more than 50% of adult bees chronically exposed to TXM. As seen in FIG. 10, the CMPs were able to reduce the number of bee deaths from 2.5% to 0.5, and from 21% to only 8% on day 2 and day 5, respectively. The inability of adult bees to climb or fly after being exposed to the TXM at 50 ppb for more than 4 hours were reduced at least 10% (FIGS. 11 &12). Thus, feeding CMPs enhances the survival rate of bees exposed to TXM and reduces the overall neuro-effect of neonicotinoids. Also, taken altogether, these results provide additional evidence that not all carbonaceous materials can act positively in bee bodies, (i.e. bees are sensitive to commercial AC and thus in some aspects, the CMPs used in the methods described herein are not activated carbon, e.g. are not commercial AC).

REFERENCES

Blacquiere, T., Smagghe, G., van Gestel, C. A. M., Mommaerts, V., 2012. Neonicotinoids in bees: a review on concentrations, side-effects and risk assessment. Ecotoxicology 21, 973-992. doi:10.1007/s10646-012-0863-x Dively, G. P., Embrey, M. S., Kamel, A., Hawthorne, D. J., Pettis, J. S., Nazzi, F., 2015. Assessment of Chronic Sublethal Effects of Imidacloprid on Honey Bee Colony Health. PLoS One 10, e0118748. doi:10.1371/journal.pone.0118748

Du Rand, E. E., Smit, S., Beukes, M., Apostolides, Z., Pirk, C. W. W., Nicolson, S. W., 2015. Detoxification mechanisms of honey bees (*Apis mellifera*) resulting in tolerance of dietary nicotine. Nat. Publ. Gr. doi:10.1038/srep11779

Fact Sheet: The Economic Challenge Posed by Declining Pollinator Populations | whitehouse.gov [WWW Document], 2014. The White House. URL https://obamawhitehouse.archives.gov/the-press-office/2014/06/20/fact-sheet-economic-challenge-posed-declining-pollinator-populations (accessed 7.23.17).

Frazier, M., Mullin, C., Frazier, J., Ashcraft, S., 2008. What Have Pesticides Got to Do with It? Am. Bee J. 148.

Gallai, N., Salles, J.-M., Settele, J., Vaissière, B. E., 2009. Economic valuation of the vulnerability of world agriculture confronted with pollinator decline. Ecol. Econ. 68, 810-821. doi:10.1016/j.ecolecon.2008.06.014

Kairo, G., Poquet, Y., Haji, H., Tchamitchian, S., Cousin, M., Bonnet, M., Pelissier, M., Kretzschmar, A., Belzunces, L. P., Brunet, J.-L., 2017. Assessment of the toxic effect of pesticides on honey bee drone fertility using laboratory and semifield approaches: A case study of fipronil. Environ. Toxicol. Chem. doi:10.1002/etc.3773

Katona, B. G., Siegel, E. G., Cluxton, R. J., 1987. The new black magic: Activated charcoal and new therapeutic uses. J. Emerg. Med. 5, 9-18. doi:10.1016/0736-4679(87)90004-7

Kunast, C., Riffel, M., De Graeff, R., Whitmore, G., 2013. Pollinators and agriculture: Agricultural productivity and pollinator protection. Brussels—Belgium.

Losey, J. E., Vaughan, M., D, N., S H, B., M H, M., P J, M., Q, T., T, S., B, C., 2006. The Economic Value of Ecological Services Provided by Insects. Bioscience 56, 311. doi:10.1641/0006-3568(2006)56[311:TEVOES]2.0.CO;2

Moritz, R. F. A., Erler, S., 2016. Lost colonies found in a data mine: Global honey trade but not pests or pesticides as a major cause of regional honeybee colony declines. Agric. Ecosyst. Environ. 216, 44-50. doi:10.1016/j.agee.2015.09.027

Morse, R. A., Calderone, N. W., 2000. The Value of Honey Bees As Pollinators of U.S. Crops in 2000 Pollination 2000—Cover The Value of Honey Bees As Pollinators of U.S. Crops in 2000. Ithaca-New York.

Park, G. D., Spector, R., Goldberg, M. J., Johnson, G. F., 1986. Expanded role of charcoal therapy in the poisoned and overdosed patient. Arch. Intern. Med. 146, 969-73.

Park, T.-J., Lee, S.-H., Simmons, T. J., Martin, J. G., Mousa, S. A., Snezhkova, E. A., Sarnatskaya, V. V., Nikolaev, V. G., Linhardt, R. J., 2008. Heparin-cellulose-charcoal composites for drug detoxification prepared using room temperature ionic liquids. Chem. Commun. 22, 5022. doi:10.1039/b809791g Peduzzi, P., Witt, R., Fernandez, R. N., Design, M. T., Ringler, L. A., 2010. UNEP Emerging Issues: Global Honey Bee Colony Disorders and Other Threats to Insect Pollinators.

Pettis, J. S., Lichtenberg, E. M., Andree, M., Stitzinger, J., Rose, R., vanEngelsdorp, D., 2013. Crop Pollination Exposes Honey Bees to Pesticides Which Alters Their Susceptibility to the Gut Pathogen *Nosema ceranae*. PLoS One 8, e70182. doi:10.1371/journal.pone.0070182

Pettis, J. S., Vanengelsdorp, D., Johnson, J., Dively, G., 2012. Pesticide exposure in honey bees results in increased levels of the gut pathogen *Nosema*. Naturwissenschaften. doi:10.1007/s00114-011-0881-1

Suliman, W., Harsh, J. B., Abu-Lail, N. I., Fortuna, A.-M., Dallmeyer, I., Garcia-Perez, M., 2016a. Modification of biochar surface by air oxidation: Role of pyrolysis temperature. Biomass and Bioenergy 85, 1-11. doi:10.1016/j.biombioe.2015.11.030

Suliman, W., Harsh, J. B., Abu-Lail, N. I., Fortuna, A.-M., Dallmeyer, I., Garcia-Perez, M., 2016b. Influence of feedstock source and pyrolysis temperature on biochar bulk and surface properties. Biomass and Bioenergy 84, 37-48. doi:10.1016/j.biombioe.2015.11.010

Tosi, S., Burgio, G., Nieh, J. C., 2017. A common neonicotinoid pesticide, thiamethoxam, impairs honey bee flight ability. Sci. Rep. 7, 1-8. doi:10.1038/s41598-017-01361-8

Wang, X.-X., Tian, K., Li, H.-Y., Cai, Z.-X., Guo, X., Kim, H., Hong, S., Wahba, L., Morazzoni, F., Song, H., Tang, J., 2015. Bio-templated fabrication of hierarchically porous $WO_3$ microspheres from lotus pollens for NO gas sensing at low temperatures. RSC Adv. 5, 29428-29432. doi:10.1039/C5RA02536B Wu-Smart, J., Spivak, M., 2016. Sub-lethal effects of dietary neonicotinoid insecticide exposure on honey bee queen fecundity and colony development. doi:10.1038/srep32108

Wu, J. Y., Anelli, C. M., Sheppard, W. S., 2011. Sub-Lethal Effects of Pesticide Residues in Brood Comb on Worker Honey Bee (*Apis mellifera*) Development and Longevity. PLoS One 6, e14720. doi:10.1371/journal.pone.0014720

Wu, J. Y., Smart, M. D., Anelli, C. M., Sheppard, W. S., 2012. Honey bees (*Apis mellifera*) reared in brood combs containing high levels of pesticide residues exhibit increased susceptibility to Nosema (Microsporidia) infection. J. Invertebr. Pathol. doi:10.1016/j.jip.2012.01.005

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of preventing or treating intoxication of a bee, comprising
   providing to the bee a comestible composition comprising carbon-rich microparticles (CMPs), wherein a surface of the CMPs is functionalized with amino and/or nitro functional groups.

2. The method of claim 1, wherein the bee is a honey bee.

3. The method of claim 2, wherein the honey bee is an *Apis mellifera* bee.

4. The method of claim 1, wherein the intoxication is caused by exposure to at least one of an herbicide, an insecticide and/or a fungicide.

5. The method of claim 4, wherein the at least one insecticide is a neonicotinoid.

6. The method of claim 5, wherein the neonicotinoid is imidacloprid, acetamiprid, clothianidin, nitenpyram, nithiazine, thiamethoxam, or thiacloprid.

7. The method of claim 1, wherein the comestible composition comprises a source of nutrition for the bees.

8. The method of claim 7, wherein the source of nutrition comprises one of more of: one or more sugars, honey, one or more proteins and one or more lipids.

9. The method of claim 1, wherein the comestible composition is in the form of a liquid, a semi-solid or a solid.

10. The method of claim 1, wherein the CMPs are carbonized bee pollen pellets or carbonized pollen grains.

* * * * *